United States Patent [19]

Munson et al.

[11] Patent Number: 4,804,489

[45] Date of Patent: Feb. 14, 1989

[54] LOW MOLECULAR WEIGHT VISCOSITY MODIFYING COMPOSITIONS

[75] Inventors: Jeffrey F. Munson, Highland Heights; Syed Q. A. Rizvi, Painesville; Stephen A. Di Biase, Euclid, all of Ohio

[73] Assignee: The Lubrizol Corporation, Wickliffe, Ohio

[21] Appl. No.: 114,902

[22] Filed: Oct. 29, 1987

[51] Int. Cl.$^4$ .................................. C01M 137/06
[52] U.S. Cl. ......................... 252/32.7 E; 252/35; 252/38; 252/46.7; 252/33
[58] Field of Search ............... 252/32.7 E, 33, 35, 252/38, 46.7, 137

[56] References Cited

U.S. PATENT DOCUMENTS

| | | | |
|---|---|---|---|
| Re. 30,142 | 11/1979 | LeSeur | 252/46.7 |
| Re. 32,235 | 8/1986 | Forsberg | 252/33 |
| 2,862,016 | 11/1958 | Sallmann et al. | 252/32.7 E |
| 2,983,678 | 5/1961 | Pellegrini, Jr. et al. | 252/32.5 |
| 2,983,679 | 5/1961 | Pellegrini, Jr. et al. | 252/32.5 |
| 3,337,456 | 8/1967 | Papayannopoulos | 252/32.5 |
| 3,450,634 | 6/1969 | Matson | 252/32.7 |
| 3,451,930 | 6/1969 | Mead | 252/32.7 |
| 3,453,124 | 7/1969 | Wurstner | 106/14 |
| 3,489,682 | 1/1970 | Le Suer | 252/32.7 |
| 3,984,448 | 10/1976 | Lyspsmeter | 252/32.7 E |
| 3,990,978 | 11/1976 | Hill | 252/8.55 R |
| 4,089,793 | 5/1978 | Meinhardt | 252/32.7 E |
| 4,104,173 | 8/1978 | Gay et al. | 252/8.55 R |
| 4,152,289 | 5/1979 | Griffin, Jr. | 252/316 |
| 4,153,649 | 5/1979 | Griffin, Jr. | 260/950 |
| 4,174,283 | 11/1979 | Griffin, Jr. | 252/8.55 R |
| 4,264,363 | 4/1981 | Cech | 106/14.28 |
| 4,308,154 | 12/1981 | Clason et al. | 252/32.7 E |
| 4,328,111 | 5/1982 | Watson et al. | 252/33.4 |
| 4,537,700 | 8/1985 | Purinton, Jr. | 252/315.1 |

*Primary Examiner*—Jacqueline V. Howard
*Attorney, Agent, or Firm*—James L. Cordek; Joseph P. Fischer; Robert A. Franks

[57] ABSTRACT

A lubricating composition is disclosed. The composition comprises
  (A) a base fluid; and
  (B) a sulfur and phosphorus containing viscosity modifying composition selected from the group consisting of a low molecular weight viscosity modifying composition and a non-polymeric viscosity modifying composition. The composition is particularly useful as a performance chemical and rheology control agent in lubricating fluids such as hydraulic fluids, transmission fluids and crankcase fluids.

25 Claims, No Drawings

4,804,489

LOW MOLECULAR WEIGHT VISCOSITY MODIFYING COMPOSITIONS

FIELD OF THE INVENTION

This invention relates to novel low molecular weight or non-polymeric viscosity modifying compositions and functional fluids containing such compositions. These compositions modify the viscosities of hydrocarbyl-based fluids including oils and formulated oils of lubricating viscosity in a fashion similar to that of polymeric viscosity improvers. Such compositions, unlike those containing polymeric viscosity improvers, possess excellent shear stability and provide outstanding low temperature viscosity performance. The compositions of this invention also have utility as antioxidants, antiwear agents, extreme pressure (EP) agents, corrosion inhibitors and deposit control additives.

BACKGROUND OF THE INVENTION

The problems associated with the lubrication of moving parts, such as in machinery, are well known to those skilled in the art. For example, in the lubrication of transmissions, proper fluid viscosity at both low and high temperatures is essential to successful operation. Good low temperature fluidity facilitates cold weather starting and ensures that the hydraulic control system will properly "shift gears". High viscosity at elevated temperatures ensures pumpability and the satisfactory functioning of converters, valves, clutches, gears and bearings.

In the operation of hydraulic fluid systems, proper fluid viscosity at both low and high temperatures is essential to successful operation and is well known in the art.

These conflicting fluidity requirements call for a product that exhibits the following characteristics:
(A) high temperature viscosity retention,
(B) low temperature fluidity, and
(C) shear stability.

In order to prepare lubricants having these characteristics, it has become common practice to add a variety of chemicals to the oil. For example, in order to meet the viscosity requirements, compositions have been added to the oils which are characterized by a relatively small change in the viscosity of the oil with changing temperature. Such oils are commonly graded according to the viscosities at low (e.g., 0° F.) and at high temperatures (e.g., 210° F.) according to SAE standards. As a result of the incorporation of such additives, the lubricating oils are often referred to as being "multigrade". In terms of widely accepted concepts such multigrade lubricants have the desirable properties of being able to function immediately, though cold, upon being put into service, and to continue to function satisfactorily as they become heated during operation.

Although chemical compositions have been developed which improve the high viscosity characteristics of lubricating oil, it is often desirable to further improve the low temperature characteristics by including compositions which function as fluidity modifiers at low temperatures. Fluidity modifiers are capable of lowering the viscosity of a lubricating oil at low temperatures generally by retarding the formation of undesirable network of microcrystalline wax substances.

In addition to the above improvements, it is desirable, if not necessary, that the lubricating compositions especially designed for use as transmission fluids and hydraulic fluids exhibit shear stability. Shear stability means that the lubricating oils will not degrade or lose their desirable viscosity characteristics as a result of the shearing forces encountered during their use. Lubricating oil compositions exhibiting desirable shear stability will be found generally to have the viscosity within 85-95% of their original viscosity after a number of hours, (e.g., 100 hours) of service. It has been recognized that many ordinary viscosity index improvers commonly added to crankcase lubricating oils, such as high molecular weight polyisobutylene and polyacrylates, do not possess the desired shear stability for use in improving the viscosity characteristics of transmission fluids and hydraulic fluids.

It now has been found that multigrade lubricants exhibiting improved shear stability and low temperature viscosity performance can be formulated by utilizing the compositions of the present invention. The compositions of this invention are particularly useful as performance chemicals and rheology control agents in lubricating fluids such as hydraulic fluids, transmission fluids and crankcase fluids.

SUMMARY OF THE INVENTION

Lubricating compositions are described which comprise a mixture of
(A) a base fluid, and
(B) a sulfur and phosphorus containing low molecular weight or non-polymeric viscosity modifying composition.

Low molecular weight or non-polymeric viscosity modifying compositions of the present invention are useful as additives in lubricating fluids such as transmission fluids and hydraulic fluids, and these formulated fluids exhibt improved shear stability while maintaining desirable high and low temperature viscosity characteristics. As an example of high temperature performance, employing about 1% of (B) causes an increase in viscosity index in 100 neutral oil by at least 150%.

DETAILED DESCRIPTION OF THE INVENTION

The first component (A) of this invention is a base fluid which is an oil of lubricating viscosity. The diverse oils of lubricating viscosity include natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halosubstituted hydrocarbon oils such as polymerized and interpolymerized olefins [e.g., polybutylenes, polypropylenes, propylene-isobutylene copolymers, chlorinated polybutylenes, poly(1-hexenes, poly(1-octenes), poly(1-decenes), etc. and mixtures thereof]; alkylbenzenes [e.g., dodecylbenzenes, tetradecylbenzenes, dinonylbenzenes, di(2-ethylhexyl)-benzenes, etc.]; polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1,000, diphenyl ether of polyethylene glycol having a molecular weight of 500-1,000, diethyl ether of polypropylene glycol having a molecular weight of 1,000-1,500, etc.) or mono- and polycarboxylic esters thereof, for example, the acetic acid esters, mixed $C_3$-$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g.,tetraethyl silicate, tetraisopropyl silicate, tetra-(2-ethylhexyl) silicate, tetra-(4-methyl-2-ethylhexyl) silicate, tetra-(p-tert-butylphenyl) silicate, hexyl-(4-methyl-2-pentoxy)-disiloxane, poly(methyl) siloxanes, poly(-methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.) polymeric tetrahydrofurans and the like.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except that they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils which have been already used in service. Such rerefined oils are also known as reclaimed or reprocessed oils and often are additionally processed by techniques directed to removal of spent additives and oil breakdown products.

The second component (B) of this invention is a sulfur and phosphorus containing low molecular weight or non-polymeric viscosity modifying composition. The low molecular weight or non-polymeric viscosity modifying composition is prepared by reacting a mono- or di hydrocarbyl hydrogen phosphite or a tri hydrocarbyl phosphite with a sulfurizing agent in the presence of a metal-containing agent.

By low molecular weight, it is meant that the weight average molecular weight ($\overline{M}w$) is not more than 10,000, preferably not more than 5,000, and most preferably not more than 2,000.

Component (B) has the general formula:

wherein R may be the same or different and is hydrocarbyl, preferably an aliphatic group containing from 1 to 30 carbon atoms. A, B, C, D and E may be the same or different and are oxygen or sulfur with the proviso that at least one must be sulfur; P is phosphorus; a, b, c and d can be 0 or 1 with the proviso that a+b is at least 1, c+d is at least 1 and a+b+c+d is at least 3. The symbol e is the combining factor for the phosphorus derived moiety. M is a metal-containing composition having a valency f where f represents the total number of metal equivalents present per equivalent of organic acid residue less one equivalent. The symbol g is the combining factor for the metal-containing composition M. Combining factors e and g are related to each other by the equation $$f \cdot g \geq e \cdot (c+d).$$

This equation states that the product of valence f and the combining factor g for metal M is equal to or greater than the analogous product of e and (c+d) for the phosphorus derived moiety. Some examples demonstrating this relationship are: When e is 1, c+d is 1, g is 1, then f is 1 or greater; when e is 2, c+d is 1, g is 1, then f is 2 or greater; when e is 1, c+d is 2, g is 2, then f is 1 or greater.

In one embodiment, A, B and D are oxygen, C is sulfur and d is zero. This embodiment is exemplified by the following structure (A)

(A)

In another embodiment, A, B and C are oxygen, D is sulfur and d is zero. This embodiment is exemplified by the following structure (B)

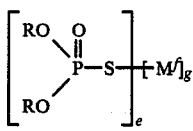
(B)

In a further embodiment, A and B are sulfur, C and D are oxygen and d is zero. This further embodiment is exemplified as follows (C)

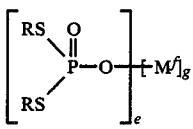
(C)

P is phosphorus, M is a metal-containing composition having a valency of 1, 2, 3 or 4; preferably M is an overbased metal-containing composition wherein the metal is selected from the group consisting of alkaline earth metals, transition metals, metalloids and mixtures thereof. The organic part of the overbased metal composition is selected from the group consisting of aliphatic and aromatic carboxylates, sulfonates, phenates, salicylates and mixtures thereof. The preferred metals are alkaline earth metals and mixtures thereof.

The mono- or di hydrocarbyl hydrogen phosphites have the formula:

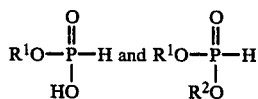

The tri hydrocarbyl phosphite has the formula

wherein the hydrocarbyl groups $R^1$ and $R^2$ are aliphatic groups containing from 1 to 30 carbon atoms, preferably 4 to 20 carbon atoms, and most preferably 4 to 12 carbon atoms.

In formula (I) and elsewhere in the disclosure and appended claims, hydrocarbyl means "hydrocarbon-based." As used herein, the term "hydrocarbon-based," "hydrocarbon-based substituent" and the like denotes a substituent having a carbon directly attached to the remainder of the molecule and having predominantly hydrocarbyl character within the context of this invention.

Examples of hydrocarbyl substituents which might be useful in connection with the present invention include the following:

(1) hydrocarbon substituents, that is, aliphatic (e.g., alkyl or alkenyl), alicyclic (e.g., cycloalkyl, cycloalkenyl) substituents, aromatic, aliphatic and alicyclic-substituted aromatic nuclei and the like as well as cyclic substituents wherein the ring is completed through another portion of the molecule (that is, for example, any two indicated substituents may together form an alicyclic radical);

(2) substituted hydrocarbon substituents, that is, those substituents containing non-hydrocarbon radicals which, in the context of this invention, do not alter the predominantly hydrocarbon character of the substituent; those skilled in the art will be aware of such radicals [e.g., halo (especially chloro and fluoro), alkoxy, mercapto, alkylmercapto, nitro, nitroso, sulfoxy, etc.];

(3) hetero atom containing substituents, that is, substituents which will, while having predominantly hydrocarbyl character within the context of this invention, contain other than carbon present in a ring or chain otherwise compose of carbon atoms. Suitable hetero atoms will be apparent to those of ordinary skill in the art and include, for example, sulfur, oxygen, nitrogen and such substituents as, e.g., pyridyl, furanyl, thiophenyl, imidazolyl, etc., are exemplary of these hetero substituents. Typically, there will be no such radicals or hetero atoms in the hydrocarbon-based substituent and it will, therefore, be purely hydrocarbon.

The hydrocarbyl phosphites useful in the present invention may be prepared by techniques well known in the art, and many hydrocarbyl phosphites are available commercially. In one method of preparation, a lower molecular weight alkyl phosphite (e.g., dimethyl) is reacted with alcohols comprising a straight-chain alcohol, a branched-chain alcohol or mixtures thereof. Each of the two types of alcohols may themselves be mixtures. Thus, the straight-chain alcohols may be a mixture of straight-chain alcohols; and the branched-chain alcohols may be a mixture of branched-chain alcohols. The higher molecular weight alcohols replace the methyl groups (analogous to classic transesterification) with the formation of methanol which is stripped from the reaction mixture.

In another embodiment, the branched-chain hydrocarbyl group can be introduced into a dialkyl phosphite by reacting the low molecular weight dialkyl phosphite such as dimethyl phosphite with a more sterically hindered branched-chain alcohol such as neopentyl alcohol (2,2-dimethyl-1-propanol). In this reaction, one of the methyl groups is replaced by a neopentyl group, and, apparently because of the size of the neopentyl group, the second methyl group is not displaced by the neopentyl alcohol. Another neoalcohol having utility in this invention is 2,2,4-trimethyl-1-pentanol.

The following examples illustrate the preparation of the hydrocarbyl hydrogen phosphite which is useful in the compositions of the present invention. Unless otherwise indicated in the following examples and elsewhere in the specification and claims, all parts and percentages are by weight, and all temperatures are in degrees Centigrade.

EXAMPLE A

A mixture of 911.4 parts (7 moles) of 2-ethylhexanol, 1,022 parts (7 moles) of Alfol 8-10, and 777.7 parts (7 moles) of dimethylphosphite is prepared and heated to 120° C. while sparging with nitrogen and removing methanol as a distillate. After about 6 hours, the mixture was heated to 145° C. and maintained at this temperature for an additional 6 hours whereupon about 406 parts of distillate are recovered. The reaction mixture is stripped to 150° C. at 50 mm. Hg., and an additional 40 parts of distillate are recovered. The residue is filtered through a filter aid and the filtrate is the desired mixed dialkyl hydrogen phosphite containing 9.6% phosphorus (theory, 9.7%).

EXAMPLE B

A mixture of 468.7 parts (3.6 moles) of 2-ethylhexanol, 1050.8 parts (7.20 moles) of Alfol 8-10, and 600 parts (5.4 moles) of dimethylphosphite is prepared and heated to 135° C. while purging with nitrogen. The mixture is heated slowly to 145° C. and maintained at this temperature for about 6 hours whereupon a total of 183.4 parts of distillate are recovered. The residue is vacuum stripped to 145° C. (10 mm. Hg.) and 146.3 parts of additional distillate are recovered. The residue is filtered through a filter aid, and the filtrate is the desired product containing 9.3% phosphorus (theory, 9.45%).

EXAMPLE C

A mixture of 518 parts (7 moles) of n-butanol, 911.4 parts (7 moles) of 2-ethylhexanol and 777.7 parts (7 moles) of dimethylphosphite is prepared and heated to 120° C. while blowing with nitrogen. After about 7 hours, 322.4 parts of distillate are collected and the material then is vacuum stripped (50 mm. Hg. at 140° C.) whereupon an additional 198.1 parts of distillate are recovered. The residue is filtered through a filter aid, and the filtrate is the desired product containing 12.9% phosphorus (theory 12.3%).

EXAMPLE D

A mixture of 193 parts (2.2 moles) of 2,2-dimethyl-1-propanol and 242 parts (2.2 moles) of dimethylphosphite is prepared and heated to about 120° C. while blowing with nitrogen. A distillate is removed and collected and the residue is vacuum stripped. The residue is filtered and the filtrate is the desired product containing 14.2% phosphorus.

EXAMPLE E

A dihydrocarbyl phosphite wherein the R groups are of 14 to 18 carbon atoms is prepared by reacting triphenylphosphite with an alcohol of 14 to 18 carbon atoms and water. 5500 parts (16.9 moles) of triphenylphosphite is heated to 50° C. and are added 8180 parts (33.8 moles) of a 14 to 18 carbon alcohol and 304 parts (16.9 moles) of water. The temperature is increased to 77° C. at 15 millimeters mercury, and later the temperature is increased to 177° C. at 15 millimeters mercury. The 14 to 18 carbon phosphite thus obtained has a percent phosphorus of 5.8.

EXAMPLE F

Following the same procedure as Example E, 5360 parts (20 moles) oleyl alcohol and 180 parts (10 moles) water is added to 3260 parts (10 moles) of triphenylphosphite. The product obtained has a percent phosphorus of 5.36.

EXAMPLE G

Following essentially the same procedure as Example D, 2080 parts (16 moles) isooctyl alcohol and 880 (8 moles) of dimethylphosphite are reacted. The product obtained has a percent phosphorus of 11.2.

EXAMPLE H

Following essentially the same procedure as Example D, 338 parts (2 moles) dibutylphosphite is reacted with 537 parts (2 moles) oleyl alcohol. The product obtained has a percent phosphorus of 8.6.

EXAMPLE I

Following essentially the same procedure as Example D, 660 parts (6 moles) dimethylphosphite and 1752 parts (12 moles) of Alfol 8-10 are reacted. The product obtained has a percent phosphorus of 10.3.

The sulfurizing agent that is reacted with the hydrocarbyl hydrogen phosphite in the presence of a metal-containing agent is selected from the group consisting of sulfur or sulfur dioxide, a mixture of sulfur halide and sodium sulfide, sulfur-containing hydrocarbyl compositions and mixtures thereof.

The metal-containing composition that is reacted with the mono- or di hydrocarbyl hydrogen phosphites or tri hydrocarbyl phosphite in the presence of a sulfurization agent is an overbased salt of an organic acid.

These overbased salts of organic acids are widely known to those of skill in the art and generally include metal salts wherein the amount of metal present in them exceeds the stoichiometric amount. Such salts are said to have conversion levels in excess of 100% (i.e., they comprise more than 100% of the theoretical amount of metal needed to convert the acid to its "normal" "neutral" salt). Such salts are often said to have metal ratios in excess of one (i.e., the ratio of equivalents of metal to equivalents of organic acid present in the salt is greater than that required to provide the normal or neutral salt which required only a stoichiometric ratio of 1:1). They are commonly referred to as overbased, hyperbased or superbased salts and are usually salts of organic sulfur acids, organic phosphorus acids, carboxylic acids, phenols or mixtures of two or more of any of these. As a skilled worker would realize, mixtures of such overbased salts can also be used.

The terminology "metal ratio" is used in the prior art and herein to designate the ratio of the total chemical equivalents of the metal in the overbased salt to the chemical equivalents of the metal in the salt which would be expected to result in the reaction between the organic acid to be overbased and the basic reacting metal compound according to the known chemical reactivity and stoichiometry of the two reactants. Thus, in a normal or neutral salt the metal ratio is one and in an overbased salt the metal ratio is greater than one.

The overbased salts used in this invention usually have metal ratios of at least about 1.5:1. Typically, they have ratios of at least about 12:1. Usually they have metal ratios not exceeding about 40:1. Typically salts having ratios of about 12:1 to about 20:1 are used.

The basic reacting metal compounds used to make these overbased salts are selected from the IIA, IIIA and IVB groups. Compounds of calcium, barium, magnesium, aluminum, titanium and zirconium, such as their hydroxides and alkoxides of lower alkanols, are usually used as basic metal compounds in preparing these overbased salts but others can be used as shown by the prior art incorporated by reference herein. Overbased salts containing a mixture of ions of two or more of these metals can also be used in the present invention.

These overbased salts can be of oil-soluble organic sulfur acids such as sulfonic, sulfamic, thiosulfonic, sulfinic, sulfenic, partial ester sulfuric, sulfurous and thiosulfuric acid. Generally they are salts of aliphatic substituted aromatic sulfonic acids.

The alkyl substituted aromatic or aliphatic sulfonic acids include the mono- or poly-nuclear aromatic or cycloaliphatic compounds. The oil-soluble sulfonates can be represented for the most part by the following formulae:

$$[R_x—T—(SO_3)_y]_z M_b \quad \text{(II)}$$

$$[R^3—(SO_3)_a]_d M_b \quad \text{(III)}$$

In the above formulae, M is either a metal cation as described hereinabove or hydrogen; T is a cyclic nucleus such as, for example, benzene, naphthalene, anthracene, phenanthrene, diphenylene oxide, thianthrene, phenothioxine, diphenylene sulfide, phenothiazine, diphenyl oxide, diphenyl sulfide, diphenylamine, cyclohexane, petroleum naphthenes, decahydro-naphthalene, cyclopentane, etc.: R in Formula II is an aliphatic group such as alkyl, alkenyl, alkoxy, alkoxyalkyl, carboalkoxyalkyl, etc; x is at least 1, and $R_x + T$ contains a total of at least about 15 carbon atoms, $R^3$ in Formula III is an aliphatic radical containing at least about 15 carbon atoms and M is either a metal cation or hydrogen. Examples of type of the $R^3$ radical are alkyl, alkenyl, alkoxyalkyl, carboalkoxyalkyl, etc. Specific examples of $R^3$ are groups derived from petrolatum, saturated and unsaturated paraffin wax, and polyolefins, including polymerized $C_2$, $C_3$, $C_4$, $C_5$, $C_6$, etc., olefins containing from about 15 to 7000 or more carbon atoms. The groups T, R, and $R^3$ in the above formulae can also contain other inorganic or organic substituents in addition to those enmmerated above such as, for example, hydroxy, mercapto, halogen, nitro, amino, nitroso, sulfide, disulfide, etc. In Formula II, x, y, z and b are at least 1, and likewise in Formula III, a, b and d are at least 1.

Specific examples of sulfonic acids useful in this invention are mahogany sulfonic acids; bright stock sulfonic acids; sulfonic acids derived from lubricating oil fractions having a Saybolt viscosity from about 100 seconds at 100° F. to about 200 seconds are 210° F.; petrolatum sulfonic acids; mono- and poly-wax substituted sulfonic and polysulfonic acids of, e.g., benzene, naphthalene, phenol, diphenyl ether, naphthalene disulfide, diphenylamine, thiophene, alpha-chloronaphthalene, etc.; other substituted sulfonic acids such as alkyl benzene sulfonic acids (where the alkyl group has at least 8 carbons), cetylphenol mono-sulfide sulfonic acids, dicetyl thianthrene disulfonic acids, dilauryl beta naphthyl sulfonic acid, dicapryl nitronaphthalene sulfonic acids, and alkaryl sulfonic acids such as dodecyl benzene "bottoms" sulfonic acids.

The latter acids derived from benzene which has been alkylated with propylene tetramers or isobutene trimers to introduce 1,2,3, or more branched-chain $C_{12}$ substituents on the benzene ring. Dodecyl benzene bottoms, principally mixtures of mono-and di-dodecyl benzenes, are available as by-products from the manufacture of household detergents. Similar products obtained from alkylation bottoms formed during manufacture of linear alkyl sulfonates (LAS) are also useful in making the sulfonates used in this invention.

The production of sulfonates from detergent manufacture-by-products by reaction with, e.g., $SO_3$, is well known to those skilled in the art. See, for example, the article "Sulfonates" in Kirk-Othmer "Encyclopedia of Chemical Technology", Second Edition, Vol. 19, pp. 291 at seq. published by John Wiley & Sons, N.Y. (1969).

Other descriptions of overbased sulfonate salts and techniques for making them can be found in the following U.S. Pat. Nos. 2,174,110; 2,174,506; 2,174,508; 2,193,824; 2,197,800; 2,202,781; 2,212,786; 2,213,360; 2,228,598; 2,223,676; 2,239,974; 2,263,312; 2,276,090; 2,276,297; 2,315,514; 2,319,121; 2,321,022; 2,333,568; 2,333,788; 2,335,259; 2,337,552; 2,346,568; 2,366,027; 2,374,193; 2,383,319; 3,312,618; 3,471,403; 3,488,284; 3,595,790; and 3,798,012. These are hereby incorporated by reference for their disclosures in this regard.

Also included are aliphatic sulfonic acids such as paraffin wax sulfonic acids, unsaturated paraffin wax sulfonic acids, hydroxy-substituted paraffin wax sulfonic acids, hexapropylene sulfonic acids, tetra-amylene sulfonic acids, polyisobutene sulfonic acids wherein the polyisobutene contains from 20 to 7000 or more carbon atoms, chloro-substituted paraffin wax sulfonic acids, nitroparaffin wax sulfonic acids, etc.; cycloaliphatic sulfonic acids such as petroleum naphthene sulfonic acids, cetyl cyclopentyl sulfonic acids, lauryl cyclohexyl sulfonic acids, bis-(di-isobutyl) cyclohexyl sulfonic acids, etc.

With respect to the sulfonic acids or salts thereof described herein and in the appended claims, it is intended that the term "petroleum sulfonic acids" or "petroleum sulfonates" includes all sulfonic acids or the salts thereof derived from petroleum products. A particularly valuable group of petroleum sulfonic acids are the mahogany sulfonic acids (so called because of their reddish-brown color) obtained as a by-product from the manufacture of petroleum white oils by a sulfuric acid process.

Generally Group IIA overbased salts of the above-described synthetic and petroleum sulfonic acids are typically useful in making this invention.

The carboxylic acids from which suitable overbased salts for use in this invention can be made include aliphatic, cycloaliphatic, and aromatic mono- and polybasic carboxylic acids such as the napthenic acids, alkyl- or alkenyl-substituted cyclopentanoic acids, alkyl- or alkenyl-substituted cyclohexanoic acids, alkyl- or alkenyl-substituted aromatic carboxylic acids. The aliphatic acids generally contain at least 1 carbon atom and preferably at least 12 carbon atoms. Usually they have no more than about 30 carbon atoms. Generally, if the aliphatic carbon chain is branched, the acids are more oil-soluble for any given carbon atoms content. The cycloaliphatic and aliphatic carboxylic acids can be saturated or unsaturated. Specific examples include 2-ethylhexanoic acid, a-linolenic acid, propylene-tetramer-substituted maleic acid, behenic acid, isostearic acid, pelargonic acid, capric acid, palmitoleic acid, linoleic acid, lauric acid, oleic acid, ricinoleic acid, undecylic acid, dioctylcyclopentane carboxylic acid, myristic acid, dilauryldecahydronaphthalene carboxylic acid, stearyl-octahydroindene carboxylic acid, palmitic acid, commercially available mixtures of two or more carboxylic acids such as tall oil acids, rosin acids, and the like.

A typical group of oil-soluble carboxylic acids useful in preparing the salts used in the present invention are the oil-soluble aromatic carboxylic acids. These acids are represented by the general formula:

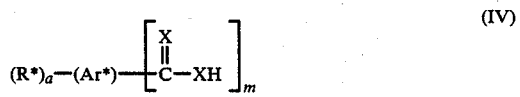

(IV)

wherein R* is an aliphatic hyrocarbon-based group of at least 4 carbon atoms, and no more than about 100 aliphatic carbon atoms, a is an integer from one to four, Ar* is a polyvalent aromatic hydrocarbon nucleus of up to about 14 carbon atoms, each X is independently a sulfur or oxygen atom, and m is an integer of from one to four with the proviso that R* and a are such that there is an average of at least 8 aliphatic carbon atoms provided by the R* groups for each acid molecule represented by Formula IV. Examples of aromatic nuclei represented by the variable Ar* are the polyvalent aromatic radicals derived from benzene, napthalene anthracene, phenanthrene, indene, fluorene, biphenyl, and the like. Generally, the radical represented by Ar* will be a polyvalent nucleus derived from benzene or naphthalene such as phenylenes and naphthylene, e.g., methylphenylenes, ethoxyphenylenes, nitrophenylenes, isopropylenes, hydroxyphenylenes, mercaptophenylenes, N,N-diethylaminophenylenes, chlorophenylenes, N,N-diethylaminophenylenes, chlorophenylenes, dipropoxynaphthylenes, triethylnaphthylenes, and similar tri-, tetra-, pentavalent nuclei thereof, etc.

The R* groups are usually hydrocarbyl groups, preferably groups such as alkyl or alkenyl radicals. However, the R* groups can contain small number substituents such as phenyl, cycloalkyl (e.g., cyclohexyl, cyclopentyl, etc.) and nonhydrocarbon groups such as nitro, amino, halo (e.g., chloro, bromo, etc.), lower alkoxy, lower alkyl mercapto, oxo substituents (i.e., =O), thio groups (i.e., =S), interrupting groups such as —NH—, —O—, —S—, and the like provided the essentially hydrocarbon character of the R* group is retained. The hydrocarbon character is retained for purposes of this invention so long as any non-carbon atoms present in the R* groups do not account for more than about 10% of the total weight of the R* groups. Examples of R* groups include butyl, isobutyl, pentyl, octyl, nonyl, dodecyl, docosyl, tetracontyl, 5-chlorohexyl, 4-ethoxypentyl, 4-hexenyl, 3-cyclohexyloctyl, 4-(p-chlorophenyl)-octyl, 2,3,5-trimethylheptyl, 4-ethyl-5-methyloctyl, and substituents derived from polymerized olefins such as polychloroprenes, polyethylenes, polypropylenes, polyisobutylenes, ethylene-propylene copolymers, chlorinated olefin polymers, oxidized ethylene-propylene copolymers, and the like. Likewise, the group Ar* may contain non-hydrocarbon substituents, for example, such diverse substituents as lower alkoxy, lower alkyl mercapto, nitro, halo, alkyl or alkenyl groups of less than 4 carbon atoms, hydroxy, mercapto, and the live. Another group of useful carboxylic acids are those of the formula:

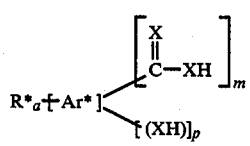
(V)

wherein R*, X, Ar*, m and a are as defined in Formula IV and p is an integer of 1 to 4, usually 1 or 2. Within this group, an especially preferred class of oil-soluble carboxylic acids are those of the formula:

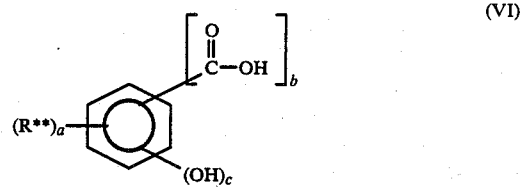
(VI)

wherein R in Formula VI is an aliphatic hydrocarbon group containing at least 4 to about 400 carbon atoms, a is an integer of from 1 to 3, b is 1 or 2, c is zero, 1, or 2 and preferably 1 with the proviso that R and a are such that the acid molecules contain at least an average of about 12 aliphatic carbon atoms in the aliphatic hydrocarbon substituents per acid molecule. And within this latter group of oil-soluble carboxylic acids, the aliphatic-hydrocarbon substituted salicylic acids wherein each aliphatic hydrocarbon substituent contains an average of at least about 16 carbon atoms per substituent and 1 to 3 substituents per molecule are particularly useful. Salts prepared from such salicylic acids wherein the aliphatic hydrocarbon substituents are derived from polymerized olefins, particularly polymerized lower 1-mono-olefins such as polyethylene, polypropylene, polyisobutylene, ethylene/-propylene copolymers and the like and having average carbon contents of about 30 to about 400 carbon atoms.

The carboxylic acids corresponding to Formulae IV-V above are well known or can be prepared according to procedures known in the art. Carboxylic acids of the type illustrated by the above formulae and processes for preparing their overbased metal salts are well known and disclosed, for example, in such U.S. Pat. Nos. as 2,197,832; 2,197,835; 2,252,662; 2,252,664; 2,714,092; 3,410,798 and 3,595,791 which are incorporated by reference herein for their disclosures of acids and methods of preparing overbased salts.

Another type of overbased carboxylate salt used in making (B) of this invention are those derived from alkenyl succinates of the general formula:

(VII)

wherein R* is as defined above in Formula IV. Such salts and means for making them are set forth in U.S. Pat. Nos. 3,271,130, 3,567,637 and 3,632,510, which are hereby incorporated by reference in this regard.

Other patents specifically describing techniques for making overbased salts of the hereinabove-described sulfonic acids, carboxylic acids, and mixtures of any two or more of these include U.S. Pat. Nos. 2,501,731; 2,616,904; 2,616,905; 2,616,906; 2,616,911; 2,616,924; 2,616,925; 2,617,049; 2,777,874; 3,027,325; 3,256,186; 3,282,835; 3,384,585; 3,373,108; 3,365,296; 3,342,733; 3,320,162; 3,312,618; 3,318,809; 3,471,403; 3,488,284; 3,595,790; and 3,629,109. The disclosures of these patents are hereby incorporated in this present specification for their disclosures in this regard as well as for their disclosure of specific suitable basic metal salts.

In the context of this invention, phenols are considered organic acids. Thus, overbased salts of phenols (generally known as phenates) are also useful in making (B) of this invention and are well known to those skilled in the art. The phenols from which these phenates are formed are of the general formula:

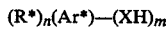    (VIII)

wherein R*, n, Ar*, X and m have the same meaning and preferences are described hereinabove with reference to Formula IV. The same examples described with respect to Formula IV also apply.

A commonly available class of phenates are those made from phenols of the general formula:

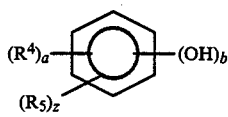    (IX)

wherein a is an integer of 1–3, b is of 1 or 2, z is 0 or 1, $R^4$ in Formula IX is a hydrocarbyl-based substituent having an average of from 4 to about 400 aliphatic carbon atoms and $R^5$ is selected from the group consisting of lower hydrocarbyl, lower alkoxyl, nitro, amino, cyano and halo groups.

One particular class of phenates for use in this invention are the overbased, Group IIA metal sulfurized phenates made by sulfurizing a phenol as described hereinabove with a sulfurizing agent such as sulfur, a sulfur halide, or sulfide or hydrosulfide salt. Techniques for making these sulfurized phenates are described in U.S. Pat. Nos. 2,680,096; 3,036,971; and 3,775,321 which are hereby incorporated by reference for their disclosures in this regard.

Other phenates that are useful are those that are made from phenols that have been linked through alkylene (e.g., methylene) bridges. These are made by reacting single or multi-ring phenols with aldehydes or ketones, typically, in the presence of an acid or basic catalyst. Such linked phenates as well as sulfurized phenates are described in detail in U.S. Pat. No. 3,350,038; particularly columns 6–8 thereof, which is hereby incorporated by reference or its disclosures in this regard.

Generally Group IIA overbased salts of the above-described carboxylic acids are typically useful in making the overbased salt of this invention.

The method of preparing metal overbased compositions in this manner is illustrated by the following examples.

EXAMPLE J

A mixture consisting essentially of 480 parts of a sodium petrosulfonate (average molecular weight of about 480), 84 parts of water, and 520 parts of mineral oil is heated at 100° C. The mixture is then heated with 86 parts of a 76% aqueous solution of calcium chloride and 72 parts of lime (90% purity) at 100° C. for two hours, dehydrated by heating to a water content of less than about 0.5%, cooled to 50° C., mixed with 130 parts of methyl alcohol, and then blown with carbon dioxide at 50° C. until substantially neutral. The mixture is then heated to 150° C. to distill off methyl alcohol and water and the resulting oil solution of the basic calcium sulfonate filtered. The filtrate is found to have a calcium sulfate ash content of 16% and a metal ratio of 2.5.

EXAMPLE K

A mixture of 1305 parts of the above carbonated calcium petrosulfonate of Example J, 930 parts of mineral oil, 220 parts of methyl alcohol, 72 parts of isobutyl alcohol, and 38 parts of amyl alcohol is prepared, heated to 35° C., and subjected to the following operating cycle four times: mixing with 143 parts of 90% commercial calcium hydroxide (90% calcium hydroxide) and treating the mixture with carbon dioxide until it has a base number of 32–39. The resulting product is then heated to 155° C. during a period of nine hours to remove the alcohol and filtered at this temperature. The filtrate is characterized by a calcium sulfate ash content of about 40% and a metal ratio of about 12.2.

EXAMPLE L

A mineral oil solution of a basic, carbonated calcium complex is prepared by carbonating a mixture of an alkylated benzene sulfonic acid (molecular weight of 470) an alkylated calcium phenate, a mixture of lower alcohols (methanol, butanol, and pentanol) and excess lime (5.6 equivalents per equivalent of the acid). The solution has a sulfur content of 1.7%, a calcium content of 12.6% and a base number of 336. To 950 grams of the solution, there is added 50 grams of a polyisobutene (molecular weight of 1000)-substituted succinic anhydride (having a saponification number of 100) at 25° C. The mixture is stirred, heated to 150° C., held at that temperature for 0.5 hour, and filtered. The filtrate has a base number of 315 and contains 35.4% of mineral oil.

EXAMPLE M

To 950 grams of a solution of a basic, carbonated, calcium salt of an alkylated benzene sulfonic acid (average molecular weight - 425) in mineral oil (base number - 406, calcium - 15.2% and sulfur - 1.4%) there is added 50 grams of the polyisobutenyl succinic anhydride of Example L at 57° C. The mixture is stirred for 0.65 hour at 55°–57° C., then at 152°–153° C. for 0.5 hour and filtered at 105° C. The filtrate has a base number of 387 and contains 43.7% of mineral oil.

EXAMPLE N

A mixture comprising 753 parts (by weight) of mineral oil, 1440 parts of xylene, 84 parts of a mixture of a commercial fatty acid mixture (acid number of 200, 590 parts of an alkylated benzene sulfonic acid (average molecular weight - 500), and 263 parts of magnesium oxide is heated to 60° C. Methanol (360 parts) and water (180 parts) are added. The mixture is carbonated at 65° C.–98° C. while methanol and water are being removed by azeotropic distillation. Additional water (180 parts) is then added and carbonation is continued at 87°–90° C. for three and a half hours. Thereafter, the reaction mixture is heated to 160° C. at 20 torr and filtered at 160° C. to give a basic, carbonated magnesium sulfonate-carboxylate complex (78.1% yield) containing 7.69% of magnesium and 1.67% of sulfur and having a base number of 336. To 950 parts of the above basic, carbonated magnesium complex, there is added 50 parts of the polyisobutenyl succinic anhydride of Example L and the mixture is heated to 150° C. for one-half hour and then filtered to give a composition having a base number of 315.

EXAMPLE O

A mixture comprising 906 grams (1.5 equivalents) of an oil solution of an alkylbenzene sulfonic acid (average molecular weight - 460–480), 564 grams of mineral oil, 600 grams of toluene, 95.7 grams of magnesium oxide (4.4 equivalents), and 120 grams of water is carbonated at a temperature of about 78°–85° C. for about 7 hours at a rate of about 3 cubic feet of carbon dioxide per hour. The carbonated product is stripped by heating to 165° C. at a pressure of 20 torr and filtered. The filtrate is an oil solution of a basic, carbonated magnesium sulfonate complex having a metal ratio of 3.1 and containing 15.27% of magnesium sulfate ash, 2.66% of sulfur and a base number of 98. To 95 grams of this complex there is added 5 grams of the polyisobutenyl succinic anhydride of Example L and the mixture is stirred at 150° C. and filtered.

EXAMPLE P

A mixture of 1000 parts (3.6 equivalents) of a tall oil fatty acid, 1799 parts of mineral oil, 292 parts isobutyl alcohol, 187 parts n-amyl alcohol and 5.3 parts calcium chloride dissolved in 240 parts water are charged to a reactor. At 40° C., 158 parts (4.27 equivalents) calcium hydroxide is added and the temperature is increased to 90° C. and held at this temperature for 1.5 hours. The contents are cooled to 50° C. and added are 73 parts isobutyl alcohol, 47 parts n-amyl alcohol, 467 parts methyl alcohol and 108 parts (2.93 equivalents) of calcium hydroxide. The contents are carbonated at 50° C. to a neutralization number to phenolphthalein of 0–5. The contents are heated to 150° C. and filtered. The filtrate has the following analyses:
Sulfate ash (%) 15.5
Metal ratio 2.0
Neutralization No. 125

EXAMPLE Q

To a mixture comprising 125 parts of low viscosity mineral oil and 66.5 parts of heptylphenol heated to about 38° C. there is added 3.5 parts of water. Thereafter, 16 parts of paraformaldehyde are added to the mixture at a uniform rate over 0.75 hour. Then 0.5 parts of hydrated lime are added and this mixture is heated to 80° C. over a 1 hour period. The reaction mixture thickens and the temperature rises to about 116° C. Then, 13.8 parts of hydrated lime are added over 0.75 hour while maintaining a temperature of about 80°–90° C. The material is then heated to about 140° C. for 6 to 7 hours at a reduced pressure of about 2–8 torr to remove substantially all water. An additional 40 parts of mineral oil are added to the reaction product and the resulting material is filtered. The filtrate is a concentrated oil solution (70% oil) of the substantially neutral calcium salt of the heptylphenol-formaldehyde condensation product. It is characterized by calcium content of about 2.2% and a sulfate ash content of 7.5%.

EXAMPLE R

To a mixture comprising 125 parts of low viscosity mineral oil and 66.5 parts of heptylphenol heated to about 38° C. there is added 3.5 parts of water. Thereafter, 16 parts of paraformaldehyde are added to the mixture at a uniform rate over 0.75 hour. Then 0.5 parts of hydrated lime are added and this mixture is heated to 80° C. over a 1 hour period. The reaction mixture thickens and the temperature rises to about 116° C. Then, 13.8 parts of hydrated lime are added over 0.75 hour while maintaining a temperature of about 80°–90° C. The material is then heated to about 140° C. for 6 to 7 hours at a reduced pressure of about 2–8 torr to remove substantially all water. An additional 40 parts of mineral oil are added to the reaction product and the resulting material is filtered. The filtrate is a concentrated oil solution (70% oil) of the substantially neutral calcium salt of the heptylphenol-formaldehyde condensation product. It is characterized by calcium content of about 2.2% and a sulfate ash content of 7.5%.

EXAMPLE S

To a reactor is added 1797 parts (6.75 equivalents) of tetrapropenyl-substituted phenol and heated to 60° C. Added is 92 parts water, 126 parts (3.4 equivalents) calcium hydroxide, 173 parts (5.4 moles) sulfur and 33.8 parts of a 50% aqueous sodium hydroxide solution. The contents are heated to reflux of 112° C. while blowing with nitrogen at 1 cfh. The contents are held at reflux for 8 hours and then stripped to 155° C. At 120° C., 719 parts oil is added and at 60° C., 133 parts (3.6 equivalents) calcium hydroxide, 66 parts (1.1 equivalents) acetic acid is added and an exotherm to 68° C. is noted. At 57° C., 965 parts methyl alcohol, 351 parts (9.5 equivalents) calcium hydroxide, and 130 parts blend oil are added. The contents are carbonated at 63°–68° C. to a neutralization number to phenolphthalein of 35–40. The contents are stripped to 155° C. while blowing with nitrogen at 1.5 cfh. At 120° C., 66 parts blend oil and 180 parts of the polyisobutenyl succinic anhydride of Example L is added. The contents are stirred for an additional hour and filtered giving a product with the following analyses:
Sulfate ash (%) 25.5
Sulfur (%) 2.52
Metal Ratio 2.30

EXAMPLE T

A reaction mixture comprising about 512 parts by weight of a mineral oil solution containing about 0.5 equivalent of a substantially neutral magnesium salt of an alkylated salicylic acid wherein the alkyl group has an average of about 18 aliphatic carbon atoms and about 30 parts by weight of an oil mixture containing about 0.037 equivalent of an alkylated benzenesulfonic acid together with about 15 parts by weight (about 0.65 equivalent) of a magnesium oxide and about 250 parts by weight of xylene is added to a flask and heated to a temperatue of about 60° C. to 70° C. The reaction mass is subsequently heated to about 85° C. and approximately 60 parts by weight of water are added. The reaction mass is held at a reflux temperature of about 95° C. to 100° C. for about 1½ hours and subsequently stripped at a temperature of 155° C.–160° C., under a vacuum, and filtered. The filtrate comprises the basic carboxylic magnesium salt characterized by a sulfated ash content of 12.35% (ASTM D-874, IP 163), indicating that the salt contains 200% of the stoichiometrically equivalent amount of magnesium.

EXAMPLE U

A reaction mixture comprising about 506 parts by weight of a mineral oil solution containing about 0.5 equivalent of a substantially neutral magnesium salt of an alkylated salicylic acid wherein the alkyl groups have an average of about 16 to 24 aliphatic carbon atoms and about 30 parts by weight of an oil mixture containing about 0.037 equivalent of an alkylate benzenesulfonic acid together with about 22 parts by weight (about 1.0 equivalent) of a magnesium oxide and about 250 parts by weight of xylene is added to a flask and heated to temperatures of about 60° C. to 70° C. The reaction is subsequently heated to about 85° C. and approximately 60 parts by weight of water are added to the reaction mass which is then heated to the reflux temperature. The reaction mass is held at the reflux temperature of about 95°–100° C. for about 1½ hours and subsequently stripped at about 155° C., under 40 torr and filtered. The filtrate comprises the basic carboxylic magnesium salt and is characterized by a sulfated ash content of 15.59% (sulfated ash) corresponding to 274% of the stoichiometrically equivalent amount.

EXAMPLE V

To a reactor is charged 1000 parts of a neutral barium sulfonate and heated to 75° C. 119 parts of barium hydroxide monohydrate is added and the contents are dried by heating to 150° C. and carbonated to obtain a neutralization number to phenolphthalein in the range of 0–1. The filtrate is an overbased barium sulfonate having the following analyses:
Sulfate ash (%) 20.0
Metal ratio 2.5
Sulfur 2.0

EXAMPLE W

A mixture consisting essentially of 4.1 parts calcium chloride dissolved in 141.6 parts water, 306.7 parts of an alcohol mixture of 61% isobutyl alcohol and 39% n-amyl alcohol and 89.3 parts calcium hydroxide are added to a reaction vessel. 1000 parts of a sulfonic acid obtained by sulfonating with sulfur trioxide, a bright stock obtained from Mobil Oil Corporation identified as Prorex 1300 is added over a 2 hour period between 50°–80° C. Volatiles are removed at 150° C. with nitrogen being passed through the system. The contents are filtered to obtain the desired product having a % calcium sulfate ash of 5.2.

EXAMPLE X

The following is charged to a reactor: a 1000 part blend of mineral oil and the product of Example W such that the calcium sulfonate content is 22%, 2.0 parts calcium chloride dissolved in 5.4 parts water, 132 parts of the mixed alcohol of Example W, 34 parts of methyl alcohol and 44 parts of the product of Example Q. The contents are stirred and 58 parts calcium hydroxide is charged and carbon dioxide is blown below the surface until the neutralization number is between 20 and 30. An additional 36 parts of calcium hydroxide is charged with carbon dioxide blowing to a neutralization number of 20–30. The contents are then dried and filtered to obtain a product with the following analyses:
Calcium sulfate ash (%) 14.6
Total base number 100
Sulfur (%) 1.3

EXAMPLE Y

The following is charged to a reactor: a 100 part blend of mineral oil and the product of Example W such that the calcium sulfonate content is 19.3%, 118.2 parts of the mixed alcohol of Example W, 2.0 parts calcium chloride dissolved in 44.1 parts methyl alcohol, 79.5 parts of the product of Example Q and 88.1 parts of calcium hydroxide. Carbon dioxide is blown at between 44°–56° C. until the neutralization number is 40–50. 5 additional portions of calcium hydroxide at 58.3 parts each are added with carbon dioxide blowing to a neutralization number of 40–50. Oil is added and the contents are stripped to 150° C. with nitrogen blowing. The analyses are:
Calcium sulfate ash (%) 38.0
Total base number 300
Sulfur (%) 0.8

The following examples illustrate the preparation of the non-polymeric viscosity modifying composition, Component (B) of this invention. In the preparation of Component (B) of this invention, for every equivalent of phosphite employed 0.5–1.2 moles of sulfurizing agent and 0.3–1.5 equivalents of metal-containing composition are employed.

EXAMPLE 1

Charged to a two-liter flask are 159 parts (0.27 equivalents) of the phosphite of Example F, 640 parts toluene, 262 parts (0.583 equivalents) of the composition of Example P and 7.8 parts (0.243 moles) sulfur. The contents are heated and stirred to about 95° C. and held at this temperature for 3 hours while passing nitrogen below the surface at 0.5 cubic feet per hour. The contents are filtered and volatiles are removed by vacuum distillation at 70° C. and 20 millimeters mercury. The liquid is the product. Analyses: percent phosphorus, 1.63; percent sulfur, 1.98; percent calcium, 2.99; neutralization number to bromophenol blue (basic), 56.

EXAMPLE 2

The procedure of Example 1 is repeated except that 144 parts (0.27 equivalents) of the phosphite of Example E replaces the phosphite of Example F. All other components and parts are the same. Analyses: percent phosphorus, 1.62; percent sulfur, 2.19; percent calcium, 3.08; neutralization number to bromophenol blue (basic), 57.

EXAMPLE 3

The procedure of Example 1 is repeated except that 52 parts (0.27 equivalents) of the dibutyl phosphite replaces the phosphite of Example F. All other components and parts are the same. Analyses: percent phosphorus, 0.493; percent sulfur, 0.61; percent calcium, 0.807; neutralization number to bromophenol blue (basic), 14.

EXAMPLE 4

The procedure of Example 1 is repeated except that 83 parts (0.27 equivalents) of the phosphite of Example G replaces the phosphite of Example F. All other components and parts are the same. Analyses: percent phosphorus, 2.38; percent sulfur, 2.43; percent calcium, 3.84; neutralization number to bromophenol blue (basic), 72.

EXAMPLE 5

The procedure of Example 1 is repeated except that 105 parts (0.27 equivalents) of the phosphite of Example H replaces the phosphite of Example F. All other components and parts are the same. Analyses: percent phosphorus, 2.2; percent sulfur, 2.3; percent calcium, 3.4; neutralization number to bromophenol blue (basic), 59.1.

EXAMPLE 6

The procedure of Example 1 is repeated except that 92 parts (0.27 equivalents) of the phosphite of Example I replaces the phosphite of Example F. All other components and parts are the same. Analyses: percent phosphorus, 0.427; percent sulfur, 0.52; percent calcium 0.661; neutralization number to bromophenol blue (basic), 11.

EXAMPLE 7

Charged to a reactor are 114 parts (0.333 equivalents) of the phosphite of Example I, 10 parts (0.3 moles) sulfur, 100 parts toluene and 337 parts (0.6 equivalents) of the overbased product of Example X. The remainder of the procedure is essentially that of Example 1. Analyses: percent phosphorus, 2.08; percent sulfur, 3.04; percent calcium, 3.06; neutralization number to bromophenol blue (basic), 54.

EXAMPLE 8

The procedure of Example 7 is followed except that 410 parts (0.6 equivalents) of the overbased product of Example J replaces the overbased product of Example X. All other components and parts are the same. Analyses: percent phosphorus, 1.78; percent sulfur, 4.42; percent calcium, 3.69; neutralization number to bromophenol blue, 51.

EXAMPLE 9

Charged to a reactor are 436 parts (0.39 equivalents) of the overbased product of Example V and 445 parts toluene. At 45° C. is charged 78 parts (0.243 moles) sulfur and at 98° C. is charged 92 parts (0.27 equivalents) of the phosphite of Example I. The procedure of Example 1 is followed to obtain the product with the following analyses: percent phosphorus, 1.54; percent sulfur, 3.25; percent barium, 8.25; neutralization number to bromophenol blue, 25.

EXAMPLE 10

Charged to a reactor are 95 parts (0.28 equivalents of the phosphite of Example I, 8 parts (0.25 moles) of sulfur, 1500 parts toluene and 194 parts (0.69 equivalents) of the overbased product of Example S. The procedure of Example 1 is followed to obtain the product with the following analyses: percent phosphorus, 2.85; percent sulfur, 4.55; percent calcium, 4.75; neutralization number to bromophenol blue, 89.

The lubricating compositions of this invention contain at least about 2% of Component (B), adjusted for any oil that might already be present. Preferably the lubricating compositions contain at least about 3% of Component (B) adjusted for any oil contained therein.

This invention also contemplates the use of other additives in combination with the composition of the invention. Such additives include, for example, auxiliary detergents and dispersants of the ash producing or ashless type, auxiliary antioxidants, auxiliary antiwear agents, seal swell agents, pour point depressing agents, viscosity improving agents, extreme pressure agents, friction modifiers, color stabilizers and anti-foam agents. Ashless dispersants and detergents are those that are substantially metal free. Such additional additives are well known in the art and are described in detail in many of the patents and other publications incorporated herein by reference.

The following table 1 details examples of lubricating oil compositions of the instant invention as well as their viscosity index results. All amounts are by weight unless indicated otherwise.

TABLE 1

| Example | Component (B) from Example | % Chemical of Component (B) | cSt at 40° C. | cSt at 100° C. | VI |
|---|---|---|---|---|---|
| I | 1 | 4 | 41.49 | 7.96 | 168 |

TABLE 1-continued

| Example | Component (B) from Example | % Chemical of Component (B) | cSt at 40° C. | cSt at 100° C. | VI |
|---|---|---|---|---|---|
| II | 2 | 4 | 42.11 | 8.95 | 201 |
| III | 3 | 4 | 61.24 | 12.38 | 205 |
| IV | 4 | 4 | 48.83 | 13.16 | >250 |
| V | 6 | 4 | 51.21 | 10.93 | 212 |
| VI | 9 | 5 | 23.6 | 4.59 | 109 |

Table 2 illustrates the difference in low temperature viscosity performance in a 75W90 commercial gear oil package containing mineral oil. Item I uses a polymethacrylate composition, and Item II is component (B) of the instant invention.

TABLE 2

| Item | Additive | % Chemical | −40° C. Brookfield Viscosity | Comment |
|---|---|---|---|---|
| I | polymethacrylate | 20 | 300,000 cP | Fails the 150,000 cP viscosity maximum requirement |
| II | Component (B) from Example 6 | 15 | 6,400 cP | Passes the 150,000 cP viscosity maximum requirement |

Data in Table 3 illustrate comparative shear stability of gear oil formulations, as determined by Manual Transaxle Test, containing the viscosity modifying composition of the instant invention and a polymethacrylate viscosity improver. The methacrylate composition shows about a 20% loss in viscosity compared with no viscosity loss for a package containing the instant invention at the end of test (EOT).

TABLE 3

| Item | Additive | % Chemical | Initial viscosity 100° C. cSt | EOT viscosity 100° C. cSt | Comment |
|---|---|---|---|---|---|
| I | polymethacrylate | 24.5 | 16.25 | 12.60 | 22.5% viscosity loss |
| II | Component (B) from Example 6 | 11.3 | 15.38 | 20.86 | No viscosity loss |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:
1. A lubricating composition which comprises:
 (A) a base fluid; and
 (B) from 2% up to 15% of a sulfur and phosphorus containing non-polymeric viscosity modifying composition of the general formula

$$[(RA)_a(RB)_b PD_c E_d]_e [M^f]_g \quad (I)$$

wherein R may be the same or different and are hydrocarbyl selected from the group consisting of $C_1$–$C_{30}$ aliphatic hydrocarbons or mixtures thereof; wherein A, B, C, D and E may be the same or different and are oxygen or sulfur, with the proviso the at least one must be sulfur; wherein P is phosphorus; wherein a, b, c and d can be zero or 1, with the proviso that a+b must be 1 or 2, c+d must be 1 or 2, and a+b+c+d must be 3, wherein e is the combining factor of a phosphorus derived moiety, wherein M is a carbonated overbased metal containing composition having a valency f where f represents the total number of metal equivalents present per equivalent of organic acid residue less one (1) equivalent; wherein g is the combining factor for the metal-containing composition with the proviso that the product of f and g are greater than or equal to the product of e and the sum of c and d.

2. A lubricating composition according to claim 1 wherein said base fluid is an oil of lubricating viscosity.

3. A lubricating composition according to claim 1 wherein the non-polymeric viscosity modifying composition has a weight average molecular weight of not more than 10,000.

4. A lubricating composition according to claim 1 wherein said non-polymeric viscosity modifying composition is prepared by reacting a hydrocarbyl hydrogen phosphite with a sulfurizing agent and a carbonated overbased metal containing composition.

5. A lubricating composition according to claim 4 wherein the hydrocarbyl hydrogen phosphite is a dihydrocarbyl hydrogen phosphite.

6. A lubricating composition according to claim 5 wherein the hydrocarbyl of said dihydrocarbyl hydrogen phosphite is selected from the group consisting of aliphatic hydrocarbons and mixtures thereof.

7. A lubricating composition according to claim 6 wherein the hydrocarbyl of said dihydrocarbyl hydrogen phosphite is selected from the group consisting of $C_4$-$C_{30}$ aliphatic hydrocarbons and mixtures thereof.

8. A lubricating composition according to claim 4 wherein said sulfurizing agent is selected from the group consisting of sulfur, sulfur halide, a mixture of hydrogen sulfide and sulfur or sulfur dioxide, a mixture of sulfur halide and sodium sulfide, sulfur containing hydrocarbyl compositions and mixtures thereof.

9. A lubricating composition according to claim 1 wherein the metal of said carbonated overbased metal containing composition is selected from the group consisting of alkali metals, alkaline earth metals, transition metals, metalloids and mixtures thereof.

10. A lubricating composition according to claim 1 wherein the metal of said carbonated overbased metal containing composition is selected from the group consisting of calcium, barium, aluminum, titanium, zirconium, magnesium, cerium and mixtures thereof.

11. A lubricating composition according to claim 1 wherein the organic part of said carbonated overbased metal containing composition is selected from the group consisting of aliphatic and aromatic carboxylates, sulfonates, phenates, salicylates and mixtures thereof.

12. A lubricating composition according to claim 1 wherein the organic part of said carbonated overbased metal containing composition is selected from the group consisting of sulfonates, aliphatic and aromatic carboxylates, salicylates and mixtures thereof.

13. A lubricating composition according to claim 1 wherein the metal of said carbonated overbased metal containing composition is selected from the group consisting of calcium, barium, aluminum, titanium, zirconium, magnesium, cerium and mixtures thereof; and, wherein the organic part of said overbased metal containing compositions is selected from the group consisting of $C_1$-$C_{30}$ aliphatic carboxylates and mixtures thereof.

14. A lubricating composition according to claim 4 wherein said hydrocarbyl hydrogen phosphite is selected from the group consisting of $C_1$-$C_{30}$ di aliphatic hydrogen phosphite and mixtures thereof; wherein said sulfurizing agent is elemental sulfur; and, wherein said metal containing composition is a carbonated overbased metal containing composition selected from the group consisting of alkaline earth $C_1$-$C_{30}$ aliphatic carboxylates and mixtures thereof.

15. A lubricating composition, according to claim 1 wherein the metal of said carbonated overbased metal containing composition is selected from the group consisting of alkali metals, alkaline earth metals, transition metals, metalloids, and mixtures thereof; and, wherein the nonmetal part of said carbonated overbased metal containing composition is selected from the group consisting of aliphatic or aromatic carboxylates, sulfonates, phenates, salicylates and mixtures thereof.

16. A lubricating composition according to claim 15 wherein the metal of said carbonated overbased metal containing composition is selected from the group consisting of alkaline earth metals and mixtures thereof.

17. A lubricating composition according to claim 15 wherein the organic part of said carbonated overbased metal containing composition is selected from the group consisting of $C_1$-$C_{30}$ aliphatic carboxylates, sulfonates and mixtures thereof.

18. A lubricating composition according to claim 15 wherein the metal of said carbonated overbased metal containing composition is selected from the group consisting of calcium, barium, aluminum, titanium, zirconium, magnesium, cerium and mixtures thereof; and wherein the organic part of said overbased metal containing composition is selected from the group consisting of $C_1$-$C_{30}$ aliphatic carboxylates and mixtures thereof.

19. An overbased sulfur and phosphorus containing low weight composition comprising:

$$[(RA)_a(RB)_b \overset{\overset{C}{\|}}{P} D_c E_d]_e [M^f]_g \quad (I)$$

wherein R may be the same or different and is hydrocarbyl; wherein A, B, C, D and E may be the same or different and are oxygen or sulfur, with the proviso that at least one must be sulfur; wherein P is phosphorus; wherein a, b, c and d can be zero or 1, with the proviso that a+b must be 1 or 2, c+d must be 1 or 2, and a+b+c+d must be 3; wherein e is the combining factor of a phosphorus derived moiety; wherein M is a carbonated overbased metal containing composition having a valency f where f represents the total number of metal equivalents present per equivalent of organic acid residue less one (1) equivalent; wherein g is the combining factor for the metal-containing composition with the proviso that the product of f and g are greater than or equal to the product of e and the sum of c and d.

20. A carbonated overbased composition according to claim 19 wherein R may be the same or different and is aliphatic; wherein A and B are oxygen; and, wherein the metal of said overbased metal containing composition is selected from the group consisting of alkali metals, alkaline earth metals, transition metals, metalloids and mixtures thereof.

21. A carbonated overbased composition according to claim 20 wherein C is sulfur; wherein D is oxygen; and wherein d is zero.

22. A carbonated overbased composition according to claim 20 wherein C is oxygen; wherein D is sulfur; and, wherein d is zero.

23. A carbonated overbased composition according to claim 19 wherein R may be the same or different and is aliphatic; wherein A and B are sulfur; and, wherein the metal of said overbased metal containing compositions is selected from the group consisting of alkali metals, alkaline earth metals, transition metals, metalloids and mixtures thereof.

24. A carbonated overbased composition according to claim 23 where C is oxygen; wherein D is oxygen; and wherein d is zero.

25. A carbonated overbased composition according to claim 19 wherein the metal of said overbased metal containing composition is selected from the group consisting of calcium, barium, aluminum, titanium, zirconium, magnesium, cerium and mixtures thereof.

* * * * *